United States Patent
Pantelidis et al.

(10) Patent No.: US 8,097,269 B2
(45) Date of Patent: *Jan. 17, 2012

(54) BIOACTIVE MATERIAL DELIVERY SYSTEMS COMPRISING SOL-GEL COMPOSITIONS

(75) Inventors: Dimitrios Pantelidis, Menlo Park, CA (US); John C. Bravman, Stanford, CA (US); Jonathan Rothbard, Sonoma, CA (US); Richard L. Klein, Santa Rosa, CA (US)

(73) Assignee: Celonova Biosciences, Inc., San Antonio, TX (US)

( * ) Notice: Subject to any disclaimer, the term of this patent is extended or adjusted under 35 U.S.C. 154(b) by 1385 days.

This patent is subject to a terminal disclaimer.

(21) Appl. No.: 11/463,237

(22) Filed: Aug. 8, 2006

(65) Prior Publication Data

US 2007/0071789 A1    Mar. 29, 2007

Related U.S. Application Data

(63) Continuation-in-part of application No. PCT/US2004/040270, filed on Dec. 1, 2004.

(60) Provisional application No. 60/764,941, filed on Feb. 2, 2006, provisional application No. 60/546,091, filed on Feb. 18, 2004.

(51) Int. Cl.
*A61F 2/02* (2006.01)

(52) U.S. Cl. .......................................... 424/425

(58) Field of Classification Search .................. None
See application file for complete search history.

(56) References Cited

U.S. PATENT DOCUMENTS

| | | |
|---|---|---|
| 5,057,296 A | 10/1991 | Beck |
| 5,102,643 A | 4/1992 | Kresge et al. |
| 5,516,781 A | 5/1996 | Morris et al. |
| 5,622,684 A | 4/1997 | Pinnavaia et al. |
| 6,054,111 A | 4/2000 | Antonietti et al. |
| 6,318,124 B1 | 11/2001 | Rutherford et al. |
| 6,334,988 B1 | 1/2002 | Gallis et al. |
| 6,365,266 B1 | 4/2002 | MacDougall et al. |
| 6,395,299 B1 | 5/2002 | Babich et al. |
| 6,458,310 B1 | 10/2002 | Liu |
| 6,465,365 B1 | 10/2002 | Annapragada |
| 6,511,658 B2 | 1/2003 | Mattai et al. |
| 6,541,539 B1 | 4/2003 | Yang et al. |
| 6,592,764 B1 | 7/2003 | Stucky et al. |
| 6,592,980 B1 | 7/2003 | MacDougall et al. |
| 6,592,991 B1 | 7/2003 | Wiesner et al. |
| 6,730,064 B2 | 5/2004 | Ragheb et al. |
| 6,991,802 B1 | 1/2006 | Ahola et al. |

(Continued)

FOREIGN PATENT DOCUMENTS

EP    0872447 A1    10/1998

(Continued)

OTHER PUBLICATIONS

Kortesuo, P., et al., "Sol-gel—processed sintered silica xerogel as a carrier in controlled drug delivery", pp. 163-167, copyright 1999 John Wiley & Sons Inc.

(Continued)

*Primary Examiner* — Carlos Azpuru
(74) *Attorney, Agent, or Firm* — Rissman Hendricks & Oliverio LLP

(57) ABSTRACT

Implantable medical devices employing a sol-gel composition coatings that functions as a bioactive material reservoir, and the use of sol-gel composition coatings for improved adhesion of organic and inorganic substrates are disclosed.

16 Claims, 7 Drawing Sheets

U.S. PATENT DOCUMENTS

| | | |
|---|---|---|
| 2002/0164380 A1 | 11/2002 | Ma et al. |
| 2006/0051397 A1 | 3/2006 | Maier et al. |
| 2006/0062820 A1 | 3/2006 | Gertner et al. |
| 2006/0115512 A1 | 6/2006 | Peacock, III et al. |

FOREIGN PATENT DOCUMENTS

| | | |
|---|---|---|
| WO | 98/34723 A2 | 8/1998 |
| WO | 99/36357 A1 | 7/1999 |
| WO | 99/47570 A1 | 9/1999 |
| WO | 00/66190 A1 | 4/2000 |
| WO | 00/25841 A1 | 5/2000 |
| WO | 00/29501 A1 | 5/2000 |
| WO | 01/15751 | 3/2001 |
| WO | 01/28529 A1 | 4/2001 |
| WO | 02/058775 A2 | 8/2002 |
| WO | 03/055534 A1 | 7/2003 |
| WO | 2005/000740 A2 | 1/2005 |
| WO | 2005/082277 | 9/2005 |

OTHER PUBLICATIONS

Beck JS, et al., "A new family of mesoporous molecular sieves prepared with liquid crystal templates." J. Am. Chem. Soc, 1992, 114:10834-10843.

Brinker CJ, et al., "Evaporation-induced self-assembly: nanostrucutres made easy." Advanced Materials, 1999, 11 (7):579-585.

Kresge CT, et al., "Ordered mesoporous molecular sieves synthesized by a liquid crystal template mechanism." Nature, Oct. 1992, 359:710-712.

Vallet-Regi M, et al., "A new property of MCM-41: drug delivery system." Chem. Mater., 2001, 13:308-311.

Munoz B, et al., "MCM-41 organic modification as drug delivery rate regulator." Chem. Mater., 2003, 15:500-503.

Schmidt-Winkel P, et al., "Microemulsion templating of siliceous mesostructured cellular foams with well-defined ultralarge mesopores." Chem. Mater., 2000, 12:686-696.

Khushalani D, et al., "Metamorphic materials: restructuring siliceous mesoporous materials." Advanced Materials, 1995, 7:842-846.

Galarneau A, et al., "Microporosity and connections between pores in SBA-15 mesostructured silicas as a function of the temperature of synthesis." New J. Chem., 2003, 27:73-79.

Xia Y, et al., "Soft lithography." Angew. Chem. Intl. Ed., 1998, 37:550-575.

Trau M, et al., "Miroscopic patterning of orientated mesoscopic silica through guided growth." Nature, 1997, 390:674-676.

Holland BT, et al., "Synthesis of macroporous minerals with highly ordered three-dimensional arrays of spheroidal voids." Science, 1998, 281:538-540.

Imhof A, et al., "Ordered macroporous materials by emulsion templating." Nature, 1997, 389:948-951.

Yang P, et al., "Hierarchically ordered oxides." Science, 1998, 282:2244-6.

Schuth, In: Studies in Surface Science and Catalysis, Galarneau A, et al (eds.), Proceedings of the 13th Internaltional Zeolite Conference, Montpellier, France, 2001, 135:1-12.

Doadrio AL, et al., "Mesoporous SBA-15 HPLC evaluation for controlled genamicin drug delivery." Journal of Controlled Release, 2004, 97(1):125-132.

Mal NK, et al., "Photocontrolled reversible release of guest molecules from coumarin-modified mesoporous silica." Nature, Jan. 2003, 242:350-353.

Axel DI, et al., "Paclitaxel inhibits arterial smooth muscle proliferation and migration in vitro and in vivo using local drug delivery." Circulation, 1997, 96:636-645.

Drachman DE, et al., "Neointimal thickening after stent delivery of paclitaxel: change in composition and arrest of growth over six months." J. Am. Coll. Cardiol., 2000, 36:2325-2332.

Grube E, et al., "High-dose 7-hexanoyltaxol-eluting stent with polymer sleeves for coronary revascularization: one-year results from the SCORE randomized trial." J. Am. Coll. Cardiol., 2004, 44:1368-72.

Kortesuo P, "Sol-gel-processed sintered silica xerogel as a carrier in controlled drug delivery." Journal of Biomedical Materials Research, 1999, 44:162-7.

Heldman AW, et al., "Paclitaxel stent coating inhibits neointimal hyperplasia at 4 weeks in a porcine model of coronary restenosis." Circulation, 2001, 103:2289-2295.

Dauskardt RH, et al., "Adhesion and debonding of multi-layer thin film structures." Engineering Fracture Mechanics, 1998, 61:141-162.

Kortesuo, P., "Sol-Gel Derived Silica Gel Monoliths and Microparticles as Carrier in Controlled Drug Delivery in Tissue Administration", Academic Dissertation, University of Helsinki, 2001, pp. 1-41.

BIOACTIVE MATERIAL DELIVERY SYSTEMS COMPRISING SOL-GEL COMPOSITIONS

CROSS REFERENCE TO RELATED APPLICATIONS

This application claims the benefit under 35 U.S.C. §119(e) to U.S. Provisional Patent Application No. 60/764,941, filed Feb. 2, 2006 and is a continuation-in-part of International Patent Application No. PCT/US2004/040270 filed Dec. 1, 2004 which claims priority to U.S. Provisional Patent Application No. 60/546,091 filed Feb. 18, 2004, the disclosures of which are fully incorporated by reference herein.

FIELD OF THE INVENTION

This invention is related to bioactive material-containing self-assembled sol-gel compositions. Specifically the invention relates to the use of such sol-gel compositions as drug reservoirs on implantable medical devices, and also the use of such sol-gel compositions to improve adhesion between organic and inorganic surfaces.

BACKGROUND OF THE INVENTION

"Sol-gel" processes are generally used to fabricate porous materials including self-assembled films. A sol is a liquid solution containing a colloid suspension of a material of interest dissolved in an appropriate solvent. Condensation reactions between the dissolved precursor molecules result in structures (particles, branched chains, linear chains, etc.) forming within the sol. The size, growth rate and morphology of these structures depend on the kinetics of the reactions within the solvent, which in turn are determined by parameters such as solution concentration, amount of water present, the temperature and pH of the solvent, agitation of the solvent and other parameters. Given enough time, condensation reactions will lead to the aggregation of growing particles or chains until eventually, a gel is formed. The gel can be visualized as a very large number of cross-linked precursor molecules forming a continuous, macroscopic-scale, solid phase, which encloses a continuous liquid phase consisting of the remaining solution. In the final steps of the sol-gel process, the enclosed solvent is removed (generally by drying) and the precursor molecules cross-link (a process called aging) resulting in the desired solid.

Sol-gel synthesis of materials offers several advantages over other synthetic routes. These advantages can include mild processing conditions (low temperature, low pressure, mild pH), inexpensive raw materials, no need for vacuum processing or other expensive equipment, and a high level of control over the resulting structure, particularly as it pertains to porosity. Regarding shape of the final product, there is essentially no limitation, because the liquid sol can be cast in any conceivable form before allowed to gel, including monoliths, thin films, fibers and micro- or nano-scale particles.

Porosity of materials produced in sol-gel processes can be controlled in a number of different ways. In the simplest sol-gel process, no special porogen is added to the sol and the porosity of the final solid is determined by the amount of precursor branching or aggregation before gelling. Average pore size, volume and surface area of porous sol-gel compositions increase with the size of the precursor molecules prior to the sol-gel processing.

Porosity can also be manipulated by the presence of additional materials within the solvent during the sol-gel process. The incorporation of sacrificial porogens in the sol (particularly those that can be easily removed via heating or other methods), is generally viewed as an efficient method to obtain porous solids when using sol-gel processes. Historically, these efforts were focused upon the fabrication of low dielectric constant (low-k) insulating films for the microelectronics industry. Sacrificial templates can also be used to create pores in inorganic materials formed using sol-gel processes. Sacrificial templates are usually amphiphilic molecules (i.e. those having hydrophilic and hydrophobic properties) capable of self-assembling in solution. These amphiphilic molecules create a highly-ordered structure that guides the precursor molecules to co-assemble around the structure. Once the precursor molecules co-assemble around the structure, it can be removed, leaving a negative image void.

The unique properties of self-assembling template-assisted, sol-gel compositions have generated a great deal of research. For example, in 1992, a group of researchers at Mobil Oil Corporation discovered that surfactant molecules (short amphiphilic molecules) will self-assemble in an aqueous solution of soluble silica, and upon solidification of the silica substrate, the surfactant can be removed leaving a material (called "MCM-41") having a hexagonal honeycombed array of uniform mesopores (mesopores are those with a pore size of between about 2 and about 50 nm; see U.S. Pat. Nos. 5,057,296 and 5,102,643, which are fully incorporated by reference herein). MCM-41 is synthesized using a cationic surfactant, quaternary alkyltrimethylammonium salts and various silica sources, such as sodium silicates, tetraethyl orthosilicate, or silica gel, under hydrothermal conditions (Beck et al., 1992, J. Am. Chem. Soc. 114, 10834). The pore size of MCM-41 can be adjusted from about 1.6 nm up to about 10 nm by using different surfactants or altering synthesis conditions. Presently, template-assisted mesoporous materials are fabricated using two broad classes of self-assembling amphiphilic templates: short molecule surfactants (see Brinker et al. (Advanced materials 1999, 11 No. 7) and Kresge et al. (Nature Vol. 359 22 October 1992)) and triblock copolymers (see U.S. Pat. No. 6,592,764 which is incorporated by reference herein).

Porous materials made using sol-gel processes can be used to deliver bioactive materials. For example, Vallet-Regi et al. (Chem. Mater. 2001, 13, 308-311) described charging powdered MCM-41 with ibuprofen. In this case, the ibuprofen was loaded into MCM-41 by dissolving the ibuprofen in hexane and adding the MCM-41 compound to the hexane in a powdered form. Munoz et al. (Chem. Mater. 2003, 15 500-503) described an experiment which demonstrated that ibuprofen could be delivered at a different rate from two different formulations of MCM-41, one made using a 16 carbon surfactant and one made using a 12 carbon surfactant.

Prior to International Patent Application Number PCT/US2004/040270 (PCT '270), which is fully incorporated by reference herein, no reference described an implantable medical device or bioactive material delivery device comprising a triblock copolymer template-based sol-gel composition formed surface coating with substantially continuously interconnected channels designed to function as a bioactive material reservoir. Moreover, no reference described a triblock copolymer template-based sol-gel composition surface coating with bioactive material found within the coating itself before being applied to the surface of an implantable medical device as well as having substantially continuously interconnected channels that could further function as a bioactive material reservoir after being applied to the surface of an implantable medical device. Thus, the invention described in PCT '270 provided at least two additional mechanisms through which bioactive materials could be loaded onto the surface of an implantable medical device.

While the materials and methods described in PCT '270 provided a number of important benefits (described therein), there is still room for improvement in the creation of bioactive material carrying materials made with sol-gel processes. For instance, better control of bioactive material particles during sol-gel processing and after device implantation could provide a benefit in allowing more accurate control over the amount of bioactive materials within a particular sol-gel composition as well as more control over the release rate of bioactive materials from an implanted medical device into the physiological environment after device implantation. The present invention provides such benefits. Before describing these benefits in more detail, however, background relating to a further aspect of the present invention is described.

One challenge in the field of implantable medical devices has been adhering bioactive materials and bioactive material-containing coatings to the surfaces of implantable devices so that the bioactive materials will be released over time once the device is implanted. One approach to adhering bioactive materials to substrates, such as the surface of implantable medical devices has been to include the bioactive materials in polymeric coatings. Polymeric coatings can hold bioactive materials onto the surface of implantable medical devices, and release the bioactive materials via degradation of the polymer or diffusion into liquid or tissue (in which case the polymer is non-degradable). While polymeric coatings can be used to adhere bioactive materials to implanted medical devices, there are problems associated with their use. One problem is that adherence of a polymeric coating to a substantially different substrate, such as a stent's metallic substrate, is difficult due to differing characteristics of the materials (such as differing thermal expansion properties). Further, most inorganic solids are covered with a hydrophilic native surface oxide that is characterized by the presence of surface hydroxyl groups (M-OH, where M represents an atom of the inorganic material, such as silicon or aluminum). At ambient conditions then, at least a monolayer of adsorbed water molecules covers the surface, forming hydrogen bonds with these hydroxyl groups. Therefore, due to this water layer, hydrophobic organic polymers cannot spontaneously adhere to the surface of the implantable medical device. Furthermore, even if polymer/surface bonds (including covalent bonds) are formed under dry conditions, those bonds are susceptible to hydrolysis (i.e. breakage) upon exposure to water. This effect is particularly important in applications where devices or components containing organic/inorganic interfaces must operate in aqueous, corrosive environments such as a human or other animal's body. These difficulties associated with adhering two different material types often leads to inadequate bonding between the implantable medical device and the overlying polymeric coating which can result in the separation of the materials over time. Such separation is an exceptionally undesirable property in an implanted medical device.

Two different approaches have traditionally been followed to reinforce organic/inorganic interfaces. The first is the introduction of controlled roughness or porosity on an inorganic surface that induces polymer mechanical interlocking. The second is chemical modification of the inorganic surface via amphiphilic silane coupling agents that improve polymer wetting, bonding and interface resistance to water. While these methods provide some benefits, they are not effective in all circumstances. Thus, there is room for improvement in methods associated with adhering inorganic and organic surfaces. Certain sol-gel composition embodiments according to the present invention provide such improvements.

SUMMARY OF THE INVENTION

The present invention provides methods of creating sol-gel compositions with enhanced bioactive material incorporation and methods to further control the rate of bioactive material release into the physiological environment from medical devices during clinical use. The methods also provide for enhanced adhesion between inorganic and organic substrates and materials. These methods provide sol-gel compositions that can be used as sustained-release bioactive material reservoirs and/or as bioactive material coatings on implantable medical devices. The present invention allows for enhanced bioactive material incorporation by modifying the chemical environment during sol-gel processing which alters the hydrophobicity or hydrophilicity of the forming material (among other characteristics), which affects how bioactive material molecules interact with the forming material and its chemical environment during sol-gel processing. Modification of the chemical environment during sol-gel processing can also affect the characteristics of the formed material after removal from the sol-gel environment in such a way to affect the release rate of bioactive materials into the physiological environment once implanted in a patient. Specifically, depending on the characteristics of a particular bioactive material, the chemical environment of the sol-gel process is adjusted to control how the bioactive materials will interact with the environment during the sol-gel process. As a non-limiting example, the addition of an organically modified silane to the sol-gel mixture can increase the hydrophobicity of the forming gel (meaning the structure forming during sol-gel processing). Without being bound by theory, it is believed that an increase in the hydrophobicity of the forming gel will impede the bioactive material's ability to move between the forming gel and the aqueous environment during sol-gel processing, holding the bioactive material more tightly to the forming gel, leading to better retention of the bioactive material within the forming sol-gel composition. Further, the enhanced hydrophobic content of the ultimately formed material can better control the rate of release of bioactive materials into the physiological environment once implanted in a patient. Methods according to the present invention can even further enhance the ability to control bioactive material release into the physiological environment following device implantation by treating the surface of a formed sol-gel composition with an organically modified silane. The hydrophobic trimethyl group of an organically modified silane can help to prevent liquids in the physiological environment of the implanted medical device from diffusing into the composition and solubilizing the bioactive materials causing their early release.

The sol-gel compositions of the present invention can also enhance adhesion to a substrate by providing pores in the form of continuously interconnected channels that allow for strong interdigitation between inorganic substrates and organic coatings.

Specifically, one embodiment according to the present invention includes a medical device comprising a structural element and a bioactive material reservoir, wherein the bioactive material reservoir comprises a coating applied to the surface of the structural element, wherein the coating comprises one or more layers wherein at least one of the layers comprises a matrix composition formed using a sol-gel process wherein the environment of the sol-gel process was tailored to the characteristics of a bioactive material to be incorporated into the matrix composition, the tailoring affecting the amount of the bioactive material within the matrix composition once formed and/or the rate of release of the bioactive material into the physiological environment once implanted in a patient. Matrix compositions can comprise, without limitation, a material selected from the group consisting of a sol-gel derived inorganic oxide; a sol-gel derived organically modified silane; a hybrid oxide comprising an organically modified silane; and an oxide having mesopores created using a template.

In certain embodiments, matrix compositions according to the present invention will comprise an inorganic oxide fabricated via the above described sol-gel process. The inorganic oxide can be selected from the group consisting of an oxide of silicon and an oxide of titanium. The matrix composition can also be a mesoporous inorganic oxide. Mesoporous inorganic oxides can be obtained using a sacrificial pore-generating template component and a self-assembly or guided-assembly fabrication process. The template component can be selected from the group consisting of an amphiphilic block copolymer, an ionic surfactant, and a non-ionic surfactant. The template component can also be a polyethylene oxide/polypropylene oxide/polyethylene oxide triblock copolymer.

Mesoporous inorganic oxides according to the present invention can comprise substantially continuous interconnected channels. The inner surfaces of the substantially continuous interconnected channels can be coated or compounded with an agent, such as an organically modified silane, that modifies a characteristic of the mesoporous inorganic oxide selected from the group consisting of hydrophobicity, charge, biocompatibility, mechanical properties, bioactive material affinity, storage capacity, and combinations thereof. Further, one or more bioactive materials can be loaded into the interconnected channels after the coating is applied to the surface of the structural element.

In certain embodiments according to the present invention, the oxide of the matrix composition can be compounded with an agent that modifies a characteristic of the oxide selected from the group consisting of hydrophobicity, charge, biocompatibility, mechanical properties, bioactive material affinity, storage capacity and combinations thereof. In one embodiment, the modifying agent is an organically modified silane. Organically modified silences can be selected from the group consisting of alkylsilanes; methyltrimethoxysilane; methyltriethoxysilane; dimethyldiethoxysilane; trimethylethoxysilane; vinyltrimethoxysilane; vinyltriethoxysilane; ethyltriethoxysilane; isopropyltriethoxysilane; butyltriethoxysilane; octyltriethoxysilane; dodecyltriethoxysilane; octadecyltriethoxysilane; aryl-functional silanes; phenyltriethoxysilane; aminosilanes; aminopropyltriethoxysilane; aminophenyltrimethoxysilane; aminopropyltrimethoxysilane; acrylate functional silanes; methacrylate-functional silanes; acryloxypropyltrimethoxysilane; carboxylate; phosphonate; ester; sulfonate; isocyanate; epoxy functional silanes; chlorosilanes; chlorotrimethylsilane; chlorotriethylsilane; chlorotrihexylsilane; dichlorodimethylsilane; trichloromethylsilane; N,O-Bis (Trimethylsilyl)-acetamide (BSA); N,O-Bis (Trimethylsilyl) Trifluoroacetamide (BSTFA); Hexamethyldisilazane (HMDS); N-Methyltrimethylsilyltrifluoroacetamide (MSTFA); N-Methyl-N-(t-butyldimethylsilyl)trifluoroacetamide (MTBSTFA); Trimethylchlorosilane (TMCS); Trimethylsilyimidazole (TMSI); and combinations thereof.

One embodiment according to the present invention includes a medical device comprising a structural element and a bioactive material-eluting coating, wherein the bioactive material-eluting coating comprises at least one layer applied over the surface of the medical device wherein the at least one layer is formed using a sol-gel process and comprises an organically modified silane. In certain embodiments, this at least one layer is a base coat applied to the surface of the medical device and the medical device further comprises a top coat applied over the base coat. Bioactive material-containing spheres can be found in a location selected from the group consisting of within the base coat, within the top coat, between the base coat and the top coat and combinations thereof. The bioactive material-containing spheres can comprise of a biodegradable polymer.

In one embodiment, the base coat and/or the top coat comprise a sol-gel inorganic oxide composition. In another embodiment, the base coat comprises a mesoporous oxide with substantially continuous interconnected channels.

Yet another embodiment according to the present invention includes a medical device comprising a structural element and a bioactive material-eluting coating, wherein the bioactive material-eluting coating comprises at least two layers wherein at least one of the at least two layers comprises a matrix composition formed using a sol-gel process wherein the environment of the sol-gel process was tailored to the characteristics of a bioactive material to be incorporated into the matrix composition, the tailoring affecting the amount of the bioactive material within the matrix composition once formed and/or the rate of release of the bioactive material into the physiological environment once implanted in a patient. These two layers can comprise, without limitation, a base coat and a top coat. In these embodiments according to the present invention, each layer can individually comprise a form selected from the group consisting of a sol-gel oxide layer without bioactive material; a sol-gel oxide layer with bioactive material incorporated in the oxide; a sol-gel oxide compounded with an organically modified silane without bioactive material; a sol-gel oxide compounded with an organically modified silane with bioactive material; an organically modified silane layer without bioactive material; an organically modified silane layer with bioactive material; a mesoporous oxide without bioactive material; a mesoporous oxide with bioactive material incorporated in the oxide; a mesoporous oxide with bioactive material incorporated in the oxide and additional bioactive material loaded into its interconnected channels after the mesoporous oxide is applied to the surface of the medical device; a mesoporous oxide with no bioactive material incorporated in the oxide but with bioactive material loaded into its interconnected channels after the oxide is applied to the surface of the medical device; and a collection of bioactive material-containing polymer spheres.

A further embodiment according to the present invention includes a medical device comprising a structural element and a bioactive material reservoir, wherein the bioactive material reservoir comprises a coating applied to the surface of the structural element, wherein the coating comprises a matrix composition formed using a sol-gel process wherein the environment of the sol-gel process was tailored to the characteristics of a bioactive material to be incorporated into the matrix composition, the tailoring affecting the amount of the bioactive material within the matrix composition once formed and/or the rate of release of the bioactive material into the physiological environment once implanted in a patient and wherein when the coating is applied to the surface of the structural element, the coating enhances adhesion between an inorganic surface and an organic surface selected from the group consisting of polymers, tissue, bone and combinations thereof.

Bioactive materials used in accordance with the present invention can, in one embodiment, be selected from the group consisting of an anti-restenotic agent, an anti-inflammatory agent, an HMG-COA reductase inhibitor, an antimicrobial agent, an antineoplastic agent, an angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptive, an analgesic, a bone growth factor, a bone remodeling factor, a neurotransmitter, a nucleic acid, an opiate antagonist and combinations thereof. Bioactive materials can also be is selected from the group consisting of paclitaxel, rampamycin, everolimus, tacrolimus, sirolimus, des-aspartate angiotensin 1, nitric oxide, apocynin, gamma-tocopheryl, pleiotrophin, estradiol, aspirin, atorvastatin, cerivastatin, fluvastatin, lovastatin, pravastatin, rosuvastatin, simvastatin, and combinations thereof.

Medical devices of the present invention can include, without limitation, a vascular conduit, a stent, a plate, a screw, a spinal cage, a dental implant, a dental filling, a brace, an artificial joint, an embolic device, a ventricular assist device, an artificial heart, a heart valve, a venous filter, a staple, a clip, a suture, a prosthetic mesh, a pacemaker, a pacemaker lead, a defibrillator, a neurostimulator, a neurostimulator lead, an implantable sensor, and an external sensor.

DEFINITION OF TERMS

Figure 1:
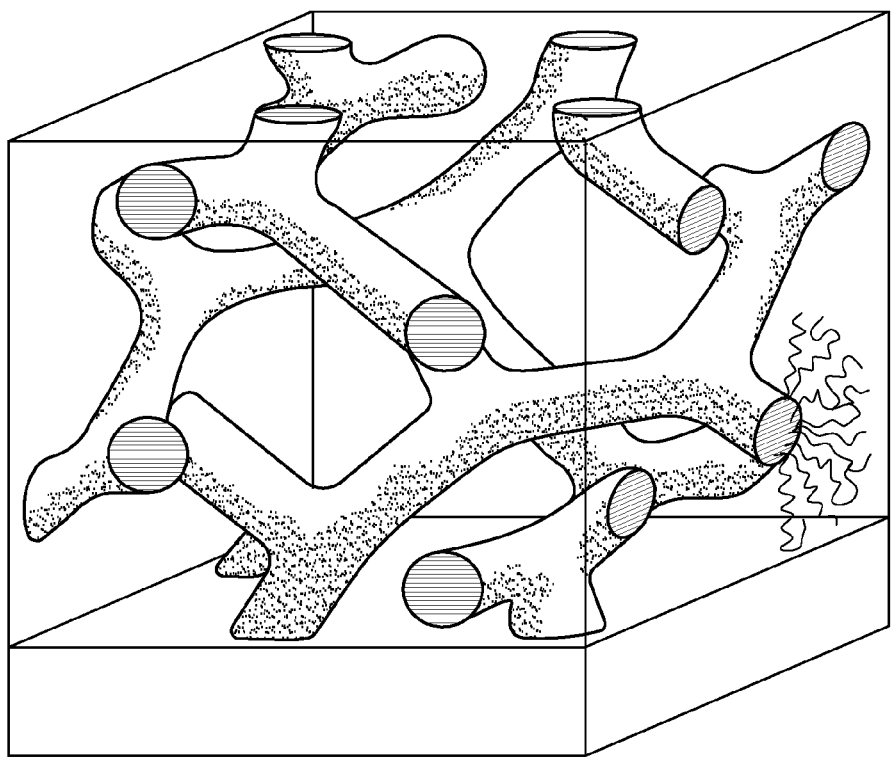
FIG. 1 shows a schematic representation of one attainable template structure with cubic symmetry.

The term "implantable medical device" refers to an entity not produced by an organism's body, which performs a function inside or on the surface of the organism's body. Implantable medical devices include but are not limited to: biomaterials, bioactive material delivery apparatuses, vascular conduits, stents, plates, screws, spinal cages, dental implants, dental fillings, braces, artificial joints, embolic devices, ventricular assist devices, artificial hearts, heart valves, venous filters, staples, clips, sutures, prosthetic meshes, pacemakers, pacemaker leads, defibrillators, neurostimulators, neurostimulator leads, and implantable or external sensors. Implantable medical devices are not limited by size and include micromechanical systems and nanomechanical systems. Embodiments of the invention include such implantable medical devices.

The terms "reservoir" or "bioactive material reservoir" refer not only to a space that can hold bioactive materials, but also to a coating that comprises a sol-gel matrix composition wherein the matrix composition encapsulates one or more bioactive materials and wherein the reservoir or bioactive material reservoir can be applied to the surface of a substrate including, in one example, an implantable medical device.

The term "bioactive material(s)" as used herein refers to any organic, inorganic, or living agent that is biologically active or relevant. For example, a bioactive material can be a protein, a polypeptide, a polysaccharide (e.g. heparin), an oligosaccharide, a mono- or disaccharide, an organic compound, an organometallic compound, or an inorganic compound. It can include a biologically active molecule such as a hormone, a growth factor, a growth factor-producing virus, a growth factor inhibitor, a growth factor receptor, an anti-inflammatory agent, an antimetabolite, an integrin blocker, or a complete or partial functional insense or antisense gene. It can also include a man-made particle or material, which carries a biologically relevant or active material. An example is a nanoparticle comprising a core with a drug and a coating on the core. Such nanoparticles can be post-loaded into pores or co-deposited with metal ions.

Bioactive materials also can include drugs such as chemical or biological compounds that can have a therapeutic effect on a biological organism. Bioactive materials include those that are especially useful for long-term therapy such as hormonal treatment. Examples include drugs for contraception and hormone replacement therapy, and for the treatment of diseases such as osteoporosis, cancer, epilepsy, Parkinson's disease and pain. Suitable biological materials can include, without limitation, an anti-restenotic agent, an anti-inflammatory agent, an HMG-COA reductase inhibitor, an antimicrobial agent, an antineoplastic agent, an angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptive, an analgesic, a bone growth factor, a bone remodeling factor, a neurotransmitter, a nucleic acid, an opiate antagonist and combinations thereof. Additional bioactive materials include, without limitation, paclitaxel, rampamycin, everolimus, tacrolimus, sirolimus, des-aspartate angiotensin I, nitric oxide, apocynin, gamma-tocopheryl, pleiotrophin, estradiol, aspirin, atorvastatin, cerivastatin, fluvastatin, lovastatin, pravastatin, rosuvastatin, simvastatin, and combinations thereof.

Bioactive materials also can include precursor materials that exhibit the relevant biological activity after being metabolized, broken-down (e.g. cleaving molecular components), or otherwise processed and modified within the body. These can include such precursor materials that might otherwise be considered relatively biologically inert or otherwise not effective for a particular result related to the medical condition to be treated prior to such modification.

Combinations, blends, or other preparations of any of the foregoing examples can be made and still be considered bioactive materials within the intended meaning herein. Aspects of the present invention directed toward bioactive materials can include any or all of the foregoing examples.

The term "sol-gel" processing refers to a process wherein a soluble precursor of a material of interest is dissolved in a liquid solvent with optional secondary materials (including, without limitation, bioactive materials) in an appropriate solvent. Condensation reactions between the dissolved precursor molecules result in structures (particles, branched chains, linear chains, etc) forming within the solution (the "sol"). The forming structures develop into the "gel" of the sol-gel process which can contain optional secondary materials within it. Once all or substantially all of the liquid solvent has been removed from the gel, certain embodiments of a matrix composition according to the present invention will have been formed.

The term "mesoporous inorganic oxide" refers to a sol-gel composition made in accordance with the methods of the present invention wherein the sol-gel composition has pores ranging in size from about 2 nm to about 50 nm.

The term "organically modified" refers to compounds that contain at least one organic (carbon-based) ligand (in one embodiment a direct metal-carbon (or semiconductor-carbon) bond).

The term "organically modified silane" refers to a compound that contains at least one non-hydrolysable carbon-based ligand bonded to silicon. This class of compounds is also referred to as ORMOSILs, silane coupling agents, silane couplers, silane adhesion promoters, or simply silanes. These compounds represent a wide variety of compounds because the non-hydrolysable ligand(s) can be any conceivable organic group(s) synthesized according to the principles of organic chemistry. Non-limiting examples include alkylsilanes (such as, but not limited to, methyltrimethoxysilane, methyltriethoxysilane, dimethyldiethoxysilane, trimethylethoxysilane, vinyltrimethoxysilane, vinyltriethoxysilane, ethyltriethoxysilane, isopropyltriethoxysilane, butyltriethoxysilane, octyltriethoxysilane, dodecyltriethoxysilane, octadecyltriethoxysilane, etc), aryl-functional silanes (e.g. phenyltriethoxysilane, etc.), aminosilanes (e.g. aminopropyltriethoxysilane, aminophenyltrimethoxysilane, aminopropyltrimethoxysilane, etc.), acrylate- and methacrylate-functional silanes (e.g. acryloxypropyltrimethoxysilane, ect), carboxylate, phosphonate, ester, sulfonate, isocyanate, and epoxy functional silanes.

It is important to realize that these compounds still contain hydrolysable groups that enable them to undergo hydrolysis/condensation reactions of sol-gel processes. Therefore, each of them or any combination of two or more of them can be used as sol-gel precursors, or they can be used in combination with a fully hydrolysable sol-gel precursor, such as tetraethoxy silane (TEOS) or titanium isopropoxide. The sol-gel composition thus obtained will not be a stoichiometric inorganic oxide. Instead it will be a hybrid sol-gel material that will exhibit bulk chemical, mechanical, physical and other properties characteristic of the particular combination of constituent components.

Exemplary organically modified silanes that can be particularly useful in this aspect include chlorosilanes; chlorotrimethylsilane; chlorotriethylsilane; chlorotrihexylsilane; dichlorodimethylsilane; trichloromethylsilane; N,O-Bis (trimethylsilyl)-acetamide (BSA); N,O-Bis (trimethylsilyl) trifluoroacetamide (BSTFA); hexamethyldisilazane (HMDS); N-methyltrimethylsilyltrifluoroacetamide (MSTFA); N-methyl-N-(t-butyldimethylsilyl)trifluoroacetamide (MTB-STFA); trimethylchlorosilane (TMCS); trimethylsilyimidazole (TMSI); and combinations thereof. This group listed as particularly useful for surface treatments is similar to compounds included in the previous paragraphs but differ in that they do not contain alkoxy ligands.

DETAILED DESCRIPTION

The present invention encompasses sol-gel compositions and their uses. Specifically the sol-gel compositions of the present invention have properties that make them useful as: (1) bioactive material reservoirs and in certain embodiments, controlled release bioactive material reservoirs, and (2) as coatings used to enhance adhesion between organic and inorganic surfaces. Methods used to produce the sol-gel compositions of the present invention can enhance the incorporation of bioactive materials into a forming gel during sol-gel processing and can also provide the formed sol-gel composition with characteristics that help control the rate of bioactive material release into the physiological environment once the composition has been implanted in a patient. Specifically, depending on the characteristics of a particular bioactive material, the chemical environment of the sol-gel process is adjusted to control how the bioactive material interacts with the environment during the sol-gel process and how it will be released from the formed composition to the physiological environment once implanted. The rate of elution of various bioactive materials entrapped in the forming gel and from the sol-gel composition once it is formed, can be more finely controlled by changing the composition of the solutions used during sol-gel processing. Further, treatment of the formed sol-gel composition with an organically modified silane can help prevent the bioactive materials from being solubilized and released from the sol-gel composition into the physiological environment after implantation.

As stated, the present invention encompasses sol-gel compositions that can be applied to the surface of an implantable medical device to function as a bioactive material reservoir or as a bioactive material coating. The sol-gel composition can be a mesoporous inorganic oxide fabricate via a template-based sol-gel synthetic route, the mesoporous material having substantially continuously interconnected channels that are adapted to act as a bioactive material reservoir capable of retaining a bioactive material and releasing it over a defined period of time. The sol-gel compositions of the present invention can act as a bioactive material reservoir by having bioactive material within the substance of the material itself before application to the surface of an implantable medical device and/or by having bioactive material loaded into the material's interconnected channels after application onto the surface of an implantable medical device. Bioactive material incorporation into the sol-gel compositions of the present invention can be enhanced or more finely controlled in one embodiment by adding an organically modified silane to the solvent during the sol-gel process. Organically modified silanes can alter the chemical environment of the sol-gel process, including the hydrophobicity/hydrophilicity of the process and the forming gel material so that the bioactive material cannot move as freely between the forming gel and aqueous environment. In one embodiment, the bioactive material is retained near the gel as it forms due to electrostatic forces and/or chemical or hydrogen bonding.

The mesoporous sol-gel compositions of the present invention exhibit a highly ordered surface-accessible pore channel network including substantially continuously interconnected channels in three dimensions throughout the film. This ordered interconnected structure provides one mechanism through which the sol-gel compositions of the present invention can act as a bioactive material reservoir. A bioactive material applied to the surface of the film will penetrate the porous film, loading the interconnected channels with bioactive materials that are later released by diffusion, osmotic or electrochemical inducement or other means.

The mesoporous sol-gel compositions of the present invention are made using a triblock copolymer template that, when mixed with a sol-gel precursor (without limitation an alkoxide silica precursor), can self-assemble into a highly-ordered 3-dimensional structure (FIG. 1). Thermal treatment (or room temperature exposure to a UV lamp/ozone source) removes the template and induces cross-linking (aging) of the surrounding inorganic phase into a mechanically robust network. Thus, a final sol-gel composition is the negative of what is shown in FIG. 1, with the block copolymer being removed to leave a network of interconnected channels. The channels so formed have predictable uniformity. In this described example, the pores and channels have diameters in the mesoscopic range, generally from about 2-30 nm and more usually from about 5-30 nm. Diameter of the channels can be precisely controlled via hydrothermal treatment or the addition of hydrophobic swelling agents in the initial solution. Thus, pores and channels of the present invention can be made to have any desired diameter including, without limitation, from about 2-100 nm, about 3-75 nm, about 5-50 nm, about 7-30 nm or about 10-20 nm.

As stated, sustained, controlled and time-release bioactive material delivery can be achieved using the sol-gel composition bioactive material delivery reservoir (and corresponding bioactive material delivery devices) of the present invention. By varying the properties of the sol-gel composition, different bioactive material delivery release rates and profiles can be achieved for various bioactive materials. For example, a bioactive material can be released with about first order or about second order kinetics. Delivery can begin upon implantation of the bioactive material delivery device, or at a particular time after implantation, and can increase rapidly from zero to a maximal rate over a short period of time, for example less than an about an hour, less than about 30 minutes, less than about 15 minutes or less than about 5 minutes. Such maximal delivery can continue for a predetermined period until the delivery rate suddenly drops. For example, delivery can continue at a maximal rate for at least about 8 hours, about 2 days, about 4 days, about 7 days, about 10 days, about 15 days, about 30 days, about 60 days or at least about 90 days. On the other hand, the bioactive material delivery rate can follow an about bell-shaped curve over time, with an initially slow but exponentially increasing delivery rate rising to a maximal rate and wherein the rate then exponentially decreases over time, finally tailing off to zero. In the field of sustained-release bioactive material delivery it is generally considered desirable to avoid a large bioactive material delivery "burst" wherein the majority of the bioactive material is delivered in a short amount of time. The methods of the present invention that allow for enhanced incorporation of bioactive material into the forming sol-gel composition can help to alleviate this problem. Embodiments adopting treating the surface and/or channels of the sol-gel composition with an organically modified silane can also be used to slow the rate of drug elution. In this approach, the hydrophobic group of the organically modified silane inhibits the ability of liquids to diffuse into the sol-gel composition and solubilize the bioactive materials leading to their early release. In accordance with the present invention then, a variety of parameters can be adjusted to produce numerous variations in delivery profiles depending on what is desirable for a particular bioactive material/disease/patient combination.

Bioactive material loading and release properties (e.g., maximum bioactive material loading, the rate of bioactive material elution, and the way the elution profile changes over time) are dependant upon the properties of both the sol-gel composition bioactive material reservoir (including whether the bioactive material is found within the material itself (pre-application to bioactive material delivery device), within the interconnected channels of the material (loaded after application to the bioactive material delivery device) or both) and the bioactive material formulation. Release kinetics can be altered by altering bioactive material formulation, changing pore size of the sol-gel materials, coating the interior of the channels, treating the surface and/or channels of the sol-gel composition with an organically modified silane and by doping the material with various substances.

There are several known methods for engineering the pore size of a sol-gel material. Pore size can be altered by altering the type of template material used and the amount used in the sol, since the size of the hydrophobic part of the amphiphilic molecule dictates, to a significant degree, the pore diameter. For example, the pore size of MCM-41 can be adjusted in a range of from about 1.6 nm up to about 10 nm (U.S. Pat. Nos. 5,057,296 and 5,102,643, and Beck et al., 1992, J. Am. Chem. Soc. 114, 10834). Another method for altering pore size is by incorporating into the sol a hydrophobic organic co-solvent that swells the hydrophobic regions after template self-assembly. The most widely used swelling agent is 1,3,5 trimethylbenzene (TMB) (Schmidt-Winkel et al., Chemistry of Materials, 2000, 12, p. 686-696), although in principle many other organic materials could play this role, such as triisopropylbenzene, perfluorodecalin, alkanes, alkenes, and long-chain amines (including N,N-dimethylhexadecylamine, trioctylamine, tridodecylamine). Other appropriate methods involve post-synthesis hydrothermal treatment of the self-assembled gel (Khushalani et al., Advanced Materials, 1995, 7, p. 842) or modifying temperature. For example, Galarneau et al., 2003 (New J. Chem. 27:73-39) demonstrates that synthesis temperature affects the structure of mesoporous substances formed in a binary way. When synthesized below 80° C., SBA-15 possesses mesopores with a diameter of about 5 nm and "ultramicropores" with a diameter of about <1 nm. When synthesized above 80° C., SBA-15 possesses mesopores with a diameter of about >9 mm and no ultramicropores.

Bioactive material release kinetics can also be altered by modifying the surface properties of the channels within the sol-gel composition. After completion of the sol-gel synthesis and removal of the structure-directing template, the interior surface of the pore channels can be modified to impart the desired surface functionality. The channels can be coated with a hydrophobic or a hydrophilic coating or with a charged surface coating to better interact with a bioactive material or other substance to be carried within the channels. One method for achieving this is by using an organically modified silane. Organically modified silanes can be used as linker agents to impart either a more hydrophobic or more hydrophilic property to a surface, depending on what termination moiety is used. If, for example, a carboxyl group is used as the termination molecule, then a hydrophilic property will be imparted, but if a long-chain fatty acid or a thyol is used, then a more hydrophobic property will be imparted. Various hydrophilic and hydrophobic moieties are well known in the art.

Alternatively, the channel walls can be modified by exposure to a $Cl_2$ working gas rendered reactive ($Cl_2 \rightarrow Cl^*$) by UV light, so that the channel surface becomes covered by chlorosilyl (Si—Cl) groups, which could then be further transformed to any desired functionality by processing according to the principles of organic chemistry. Similar results could also be obtained via, for example, initial treatment of the pore wall surface with other working gases, including phosgene (SOCl), isocyanate (—N=C=O), malamides and others. These are chemicals that would easily react with the silanol (Si—OH) groups of the pore wall surface, thus replacing the silanols with alternative groups (e.g. Si—Cl in the case of phosgene) that can then at a subsequent step be reacted upon to impart any desired chemical functionality to the pore walls.

Another way of engineering channel properties is treatment with strong acidic or basic liquid solutions to impart surface charges. Specifically, exposure to a solution with a pH lower than the isoelectric point of the surface (pI=2 for silica) results in the protonation of surface silanol moieties (Si—OH→Si—OH$^{2+}$), whereupon the surface becomes positively charged. Similarly, treatment with a solution of pH higher than the surface pI will result in deprotonation of surface silanols and a negative net surface charge (Si—OH→Si—O$^-$). It is important to note that this charge will not be sustained upon removal from the acidic or basic solution, unless the solution also contains a charged solute of opposite sign that can attach to the charged surface via electrostatic attraction. In the latter case, the surface will remain charged and the solute attached to it even after removal from the acidic or basic solution. These properties can be used to stimulate elution of polar or electrically charged bioactive molecules from a mesoporous matrix (discussed further below).

One or more of the above methods can be chosen based on the particular bioactive material or bioactive materials that will be loaded into the channels because different bioactive materials have different properties in terms of size, hydrophobicity and charge. This will influence bioactive material loading and release from a sol-gel composition. For example, paclitaxel is a hydrophobic (lipophilic) molecule of about 1-2 nm in size. Other hydrophobic bioactive materials include, for example and without limitation, most antipsychotics, antibiotics such as amphotericin, dexamethasone and flutamide. Paclitaxel is somewhat more hydrophobic than rapamycin, and corticosteroids are generally less hydrophobic than rapamycin or paclitaxel. If using a hydrophobic bioactive material it could be desirable to coat the channels with a hydrophobic coating to maximize bioactive material loading. Bioactive materials that are highly hydrophilic and water soluble, could benefit from a hydrophilic coating to maximize bioactive material loading. Hydrophilic bioactive materials include, without limitation, most hormonal peptides, antibiotics such as vancomycin, and phenobarbital, cimetidine, atenolol, aminoglycosides, hormones (e.g., thyrotropin-releasing hormone), p-nitrophenyl beta-cellopentaoside and leutinizing hormone-releasing hormone, and many others. Well known cationic bioactive materials include, without limitation, vincristine, amiloride, digoxin, morphine, procainamide, quinidine, quinine, ranitidine, triamterene, trimethoprim, vancomycin and the aminoglycosides. Anionic bioactive materials include, without limitation, penicillin and many diuretics. Thus, in determining whether a channel treatment would be beneficial, the characteristics of the bioactive material(s) to be loaded and the desired release profile should be considered.

Once within a matrix or channel according to the present invention, bioactive materials can be eluted in several ways. Simple diffusion can be used to release bioactive material, in which case the bioactive material moves down a concentration gradient into the environmental solution (body fluid). Osmotic effects can also be used whereby a dissolved bioactive material can be carried by bulk fluid flow from an area of higher to lower osmotic potential. Osmotic effects can also be used to force bioactive material from the matrix. For example, a hydrophobic bioactive material can be forced from the matrix by filling the matrix with an increasing volume of an aqueous solution. This might be done, for example, by filling half of the sol-gel matrix composition with a hydrophobic bioactive material, and partially filling the other half with a soluble salt. When implanted into a patient, water from body fluids would dissolve the salt, creating a strong osmotic potential that would draw water into the matrix. The incoming water would displace the hydrophobic bioactive material, forcing it out of the matrix into the surrounding physiological environment. Such a system could be designed in a number of ways, and the osmotic pump could be separate from the sol-gel matrix composition.

Bioactive material release kinetics can also be adjusted by altering the physical characteristics of the bioactive material formulation itself such as net charge, hydrophobicity and rheological properties of the bioactive material formulation.

Other methods used to elute a bioactive material from the sol-gel composition include the use of electrophoretic mechanisms for charged bioactive material particles, physical gating, such as controlling the surface area of the bioactive material reservoir exposed to the environment, and the use of various biodegradable and semi-permeable membranes that can be used to control the rate of release of a bioactive material from the reservoir.

One important aspect of the current invention is the delivery of anti-restenosis bioactive materials. One especially effective anti-restenosis bioactive material appears to be the lipophilic bioactive material paclitaxel (N-benzyl-beta-phenylisoserine ester, M.W. 853.9), an anti-tumor agent isolated from the bark of the yew tree.

As stated, the sol-gel compositions according to the present invention are very well suited for enhancing adhesion between organic and inorganic surfaces because of the highly ordered, open, surface-accessible channel network that is continuously interconnected throughout the entire film volume. For example, organic bioactive material-containing polymers deposited on the top surface of an inorganic sol-gel composition of the present invention can access and penetrate the porous film throughout its thickness, creating a tough nanocomposite phase that extends all the way to the underlying inorganic substrate surface. Such molecular interdigitation of the polymer and the sol-gel composition creates a very strong bond, resistant to corrosion and mechanical removal.

Figure 2:
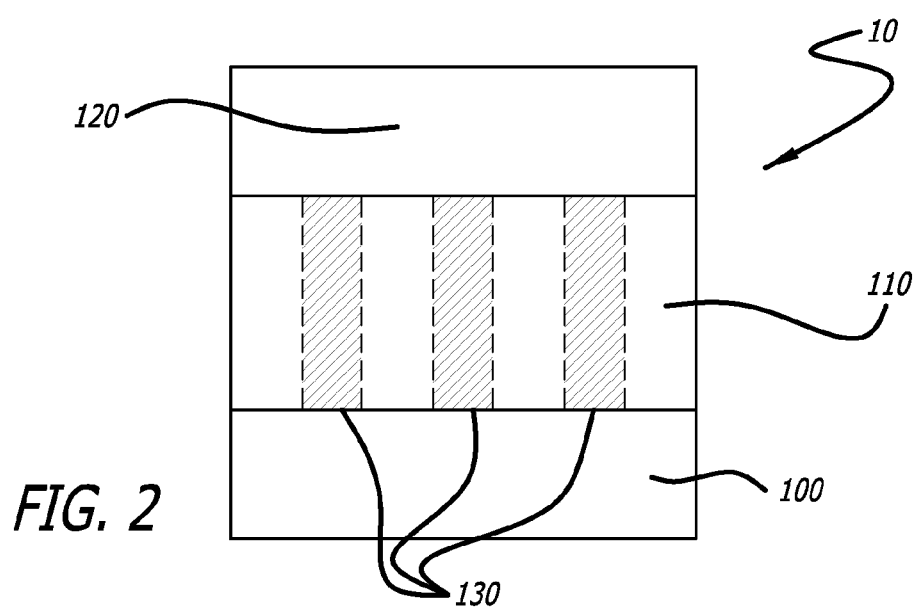
FIG. 2 shows a schematic representation of a mesoporous sol-gel $SiO_2$ film, where the pores exhibit cubic symmetry, on a substrate surface.

FIG. 2 illustrates the tri-layer structure 10 of the present invention used to enhance adhesion between organic and inorganic surfaces. In this example a sol-gel composition 110 is deposited on an inorganic substrate 100. An organic polymer 120 is interdigitated through the sol-gel composition 110. In a typical sol-gel composition of the present invention, the average diameter of the pores 130 can be between about 5-30 nm and the surface density of pores (access points to the channel network) from the film top can be on the order of about $10^{12}/cm^2$.

In using the sol-gel compositions of the present invention to enhance adhesion, the polymer to which adhesion is sought can be deposited on top of the sol-gel composition by the spin-coating of a precursor formulation or any other suitable method. The polymer material then enters the pores of the sol-gel composition by, without limitation, capillary action or pressure or thermal treatment, thereby penetrating the sol-gel composition substantially, in one embodiment through its entire thickness. This penetration is followed by cross-linking of the polymer via thermal curing, by photocontrolled reaction or other suitable methods. Optionally, this step can be accompanied or followed by formation of covalent or other chemical bonds between the organic polymer 120 and the modified walls of the pores 130 and the surface of the inorganic substrate 100 so as to further improve adhesion.

Whether for the purpose of providing a bioactive material reservoir or for enhancing adhesion, the sol-gel compositions of the present invention can be produced and deposited onto a substrate by the following non-limiting method: (1) first, a substrate is provided, for example and without limitation surgical steel, a nickel-titanium alloy (NiTi), a cobalt-chrome alloy (Co—Cr), a carbon-fiber material, a plastic or other suitable biocompatible material; (2) the substrate surface is then cleaned of any undesired contamination; (3) the substrate is microblasted; (4) the sol-gel composition is produced by mixing the inorganic precursor with amphiphilic tri-block co-polymer templating agent, one or more bioactive materials and an organically modified silane. Non-limiting examples of typical inorganic precursors include $SiO_2$ and $TiO_2$ such as tetraethoxysilane and titanium orthopropoxide. At this stage, if desired, other solvents can also be added e.g., a rheology modifier such as ethanol or the swelling agent such as 1,3,5 trimethylbenzene; and (5) the template-assisted sol-gel composition is then deposited on the surface of the substrate, generally by, without limitation, spin-coating, dip-coating or spray-coating or painting of the object to be coated. Further, in certain embodiments, the sol-gel composition can be treated on its surface or within its channels with an organically modified silane.

Appropriate organically modified silanes for use in accordance with the present invention include, without limitation, alkylsilanes (such as, but not limited to, methyltrimethoxysilane, methyltriethoxysilane, dimethyldiethoxysilane, trimethylethoxysilane, vinyltrimethoxysilane, vinyltriethoxysilane, ethyltriethoxysilane, isopropyltriethoxysilane, butyltriethoxysilane, octyltriethoxysilane, dodecyltriethoxysilane, octadecyltriethoxysilane, etc), aryl-functional silanes (e.g. phenyltriethoxysilane, etc.), aminosilanes (e.g. aminopropyltriethoxysilane, aminophenyltrimethoxysilane, aminopropyltrimethoxysilane, etc.), acrylate- and methacrylate-functional silanes (e.g. acryloxypropyltrimethoxysilane, ect), carboxylate, phosphonate, ester, sulfonate, isocyanate, epoxy functional silanes, chlorosilanes, (e.g. chlorotrimethylsilane, chlorotriethylsilane, chlorotrihexylsilane, dichlorodimethylsilane, trichloromethylsilane, etc), N,O-Bis (trimethylsilyl)-acetamide (BSA); N,O-Bis (trimethylsilyl) trifluoroacetamide (BSTFA); hexamethyldisilazane (HMDS); N-methyltrimethylsilyltrifluoroacetamide (MSTFA); N-methyl-N-(t-butyldimethylsilyl)trifluoroacetamide (MTBSTFA); trimethylchlorosilane (TMCS); trimethylsilyimidazole (TMSI); and combinations thereof.

Dip-coating or spray-coating can be easily used for coating objects with complex shapes and arbitrary curvature, such as stents. The final thickness of the sol-gel composition can be controlled and optimized by diluting the solution, specifically by adding more solvent (typically ethanol) to the solution, so that in the final working solution the concentration of all the ingredients is reduced by the same amount and their relative concentration and molar ratios remain constant. Sol-gel composition thickness can also be adjusted by changing the spin-coating or dip-coating rate, or both, as described in the examples. The template material that defines the channels is then removed by thermal treatment or by room-temperature exposure to a UV lamp/ozone source. This will remove the template and induce cross-linking of the surrounding inorganic phase into a mechanically robust network. UV/ozone treatment is particularly useful if the inorganic precursor is heat sensitive.

In certain embodiments according to the present invention patterning techniques to template the sol-gel compositions at multiple length-scales can be used. For example, coating with a sol-gel mesoporous oxide such as silica requires a hydrophilic surface with available —OH moieties that can partake in condensation reactions with the sol-gel precursor molecules. If traditional lithography, or soft lithography (Whitesides et al., Angew. Chem. Intl. Ed, 1998, 37, p. 550) or any other surface patterning method is used to strip selected surface regions of —OH functionality before deposition, the mesoporous coating would be patterned accordingly. Alternatively, the sol-gel composition coating can be patterned via, for example, micro-molding in capillaries (Trau et al., Nature. 1997, 390, p. 674) where a limited amount of the liquid sol can be compressed between a flexible silicone mold and the substrate surface.

Alternatively, a second sacrificial porogen can be employed to pattern the deposition of a sol-gel composition coating. For example, it is a well established method to create macroporous inorganic materials (100 nm<d<10 μm) by templating the sol-gel solid via commercially available or custom-synthesized latex particles, such as monodisperse polystyrene spheres with radii in the 100-500 nm range (Stein et al., Science, 1998, 281, p. 538-540) or phase-separated emulsions, such as oil in formamide systems (Pine et al., Nature, 1997, 389, p. 948-951). These and other related methods can be combined with the self-assembling template processes that generate the presently described sol-gel compositions. The end result would be hierarchically ordered inorganic solids with multi-scale porosities (Whitesides et al., Science, 1998, 282, p. 2244). Such an approach could be particularly powerful in orthopedic applications, where a macro-scale porous implant surface is desirable to allow cell migration and bone/implant integration, whereas meso-scale porosity can be exploited for local bioactive material delivery.

Another embodiment according to the present invention is the use of mesoporous materials that are relatively easy to obtain (such as silica) as intermediate molds for patterning other inorganic solids for which no appropriate sol-gel precursor exists, including noble metals such as, without limitation, gold and platinum and extending all the way to even carbon-based polymers. For example, a mesoporous silica coating could be first deposited on an implantable device, followed by "casting" via a volatile precursor or liquid-based suspension of, without limitation, Pd or Au nanoparticles, followed by dissolution of the mesoporous silica via, for example, hydrofluoric acid treatment, thus resulting in a mesoporous noble-metal replica of the silica framework (Schuth, in Studies in Surface Science and Catalysis, v.135, p. 1-12).

EXAMPLES

Example I

A 0.1M tetraethoxy silane (TEOS) sol-gel solution was prepared by first making 0.3M ethanolic hydrochloric acid in a 20 mL glass scintillation vial by mixing 25 μL of concentrated (12M) HCl with 860 μL deionized water and 3 mL of absolute ethanol. In a 1.5-mL microcentrifuge tube 1 mL of ethanol and 112 μL TEOS were combined. The TEOS solution was added dropwise to the acidified ethanol over 30 seconds and the resulting TEOS solution was allowed to hydrolyze for 45 minutes. At the end of the hydrolysis period, 2 mL of the hydrolyzed TEOS solution were added to des-aspartate angiotensin I (DAA-I) (2.5 mg) in a glass vial (1 dram). Brief sonication was used to ensure both dissolution and mixing of the peptide. The resultant solution was transferred to a 5 mL gas tight Hamilton syringe after passage through a 5 micron filter. The syringe was placed in a Harvard Scientific syringe pump and connected to the ultrasonic sprayer.

Either two cleaned 12 mm or four cleaned 6 mm stents were mounted onto the coating mandrel using grooved cones for suspension. The mandrel was attached to the spraying apparatus and the stents were sprayed with sufficient amounts of the sol-gel solution containing the DAA-I in repeated passes of the mandrel past the spray head to deposit approximately 20 μg of gel on the surface after 30 minutes of drying at 40° C. A topcoat of 0.1M TEOS was applied to serve as an additional barrier to provide a desired rate of release of the DAA-I. A 0.1M TEOS solution was prepared as previously described, but with no DAA-I added. The stents were sprayed with sufficient TEOS to result in a topcoat of 50 μg after drying for 30 minutes at 40° C.

Figure 3A:
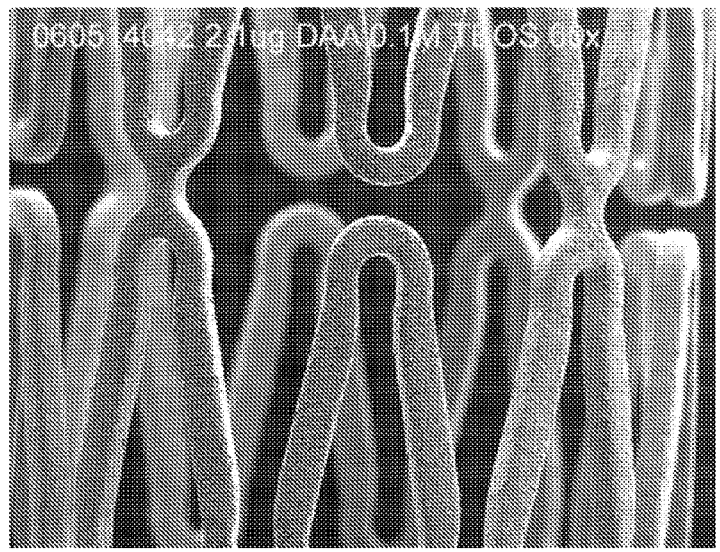
FIGS. 3A-3D show four different magnifications of SEM images of implantable medical devices coated with sol-gel compositions according to the teachings of the present invention.
Figure 3B:
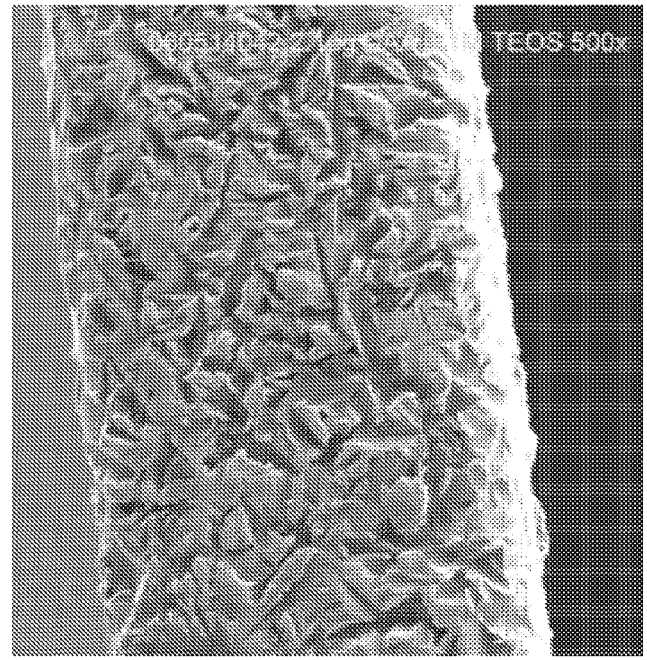
Figure 3C:
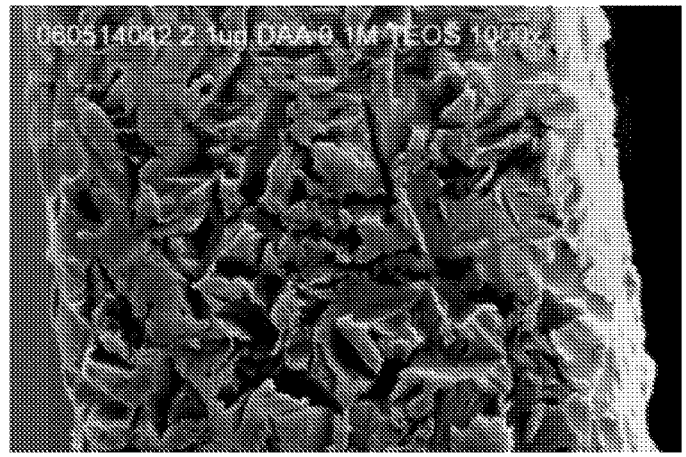
Figure 3D:
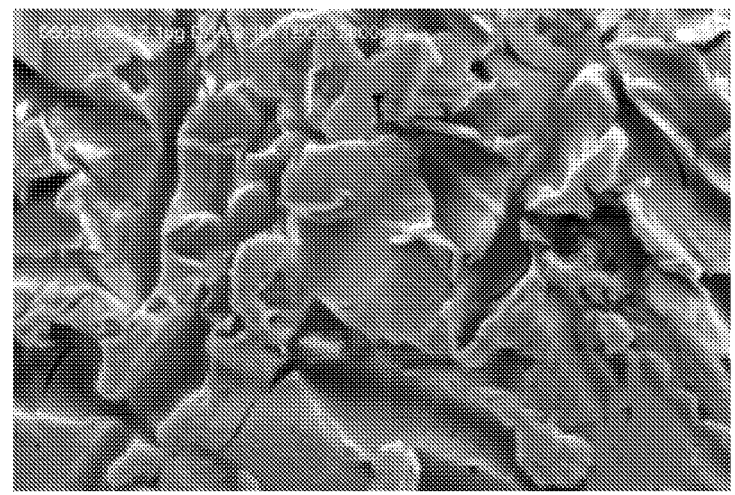

Referring to FIGS. 3A-3D, scanning electron micrographs (SEMs) of the DAA-I coated stents were captured using a Hitachi S-3000N Scanning Electron Microscope with Oxford Instruments INCA X-Sight Model 7021. Several previously DAA-I/TEOS-coated stents were placed on a rotating stage within the scanning electron microscope prior to evacuation of the chamber using double sided conducting adhesive discs. A map of the individual stents was drawn indicating location and subsequent identification based upon orientation of the individual stents to one another. No surface preparation of the stents was performed prior to imaging. Stents were oriented in the SEM field using an internal visual camera, and external controls. Upon acceptable orientation, the electronic imaging system was energized and the various areas of interest were imaged at magnifications of 60× (FIG. 3A); 500× (FIG. 3B); 1000× (FIG. 3C); and 2000× (FIG. 3D). Electronic images of specific areas of interest were captured following automatic adjustment for brightness and contrast.

Figure 4:
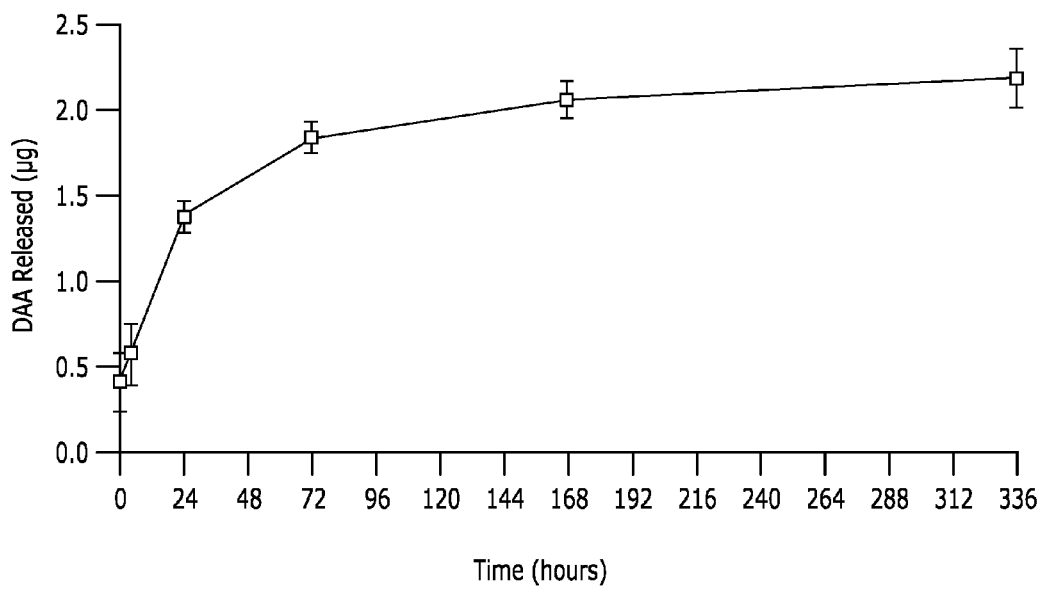
FIG. 4 shows the rate of elution of des-aspartate angiotensin I (DAA-I) from an implantable medical device coated with a sol-gel composition according to the teachings of the present invention.

Referring to FIG. 4, elution of DAA-I from the TEOS coated stents was measured by analyzing the amount of DAA-I found in 0.1% solutol in ammonium acetate buffer, pH 5.0, as a function of time, when the stents were incubated in this medium at 37° C. The amount of DAA-I was determined by integrating the DAA-I peak in high performance liquid chromatography (HPLC) profiles using a Altima C-8 column (Altech, Chicago Ill.) and comparison to standard curves. As can be seen in FIG. 4, increasing the molar ratio between TEOS and DAA-I can slow the rate of DAA-I elution.

Example II

Figure 5A:
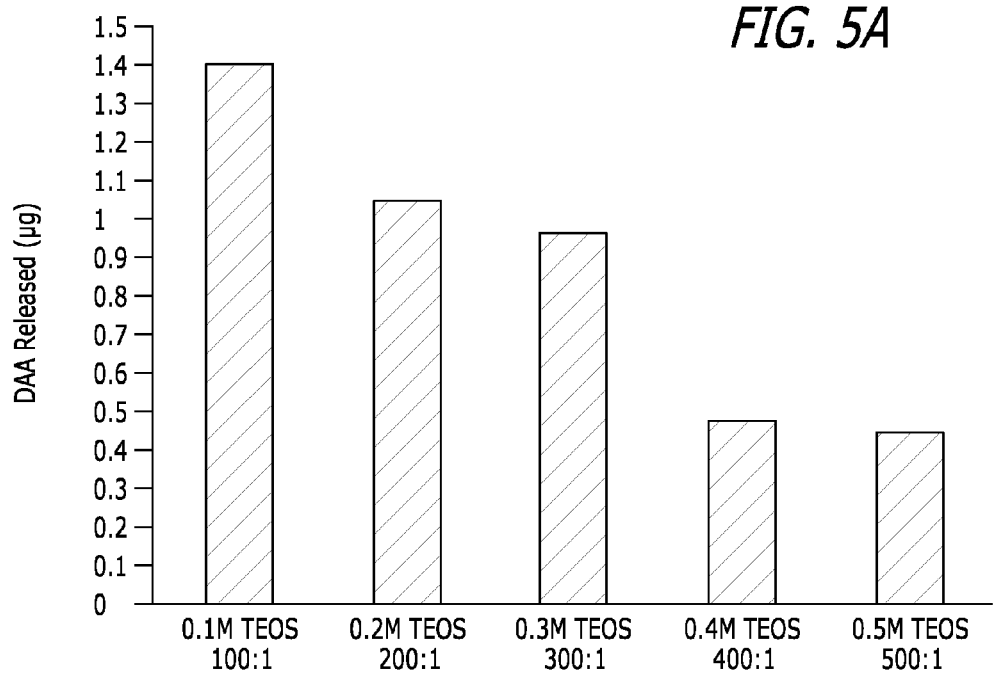
FIGS. 5A-5B show the amount of DAA-I released after 72 hours from implantable medical devices coated with sol-gel compositions according to the teachings of the present invention.
Figure 5B:
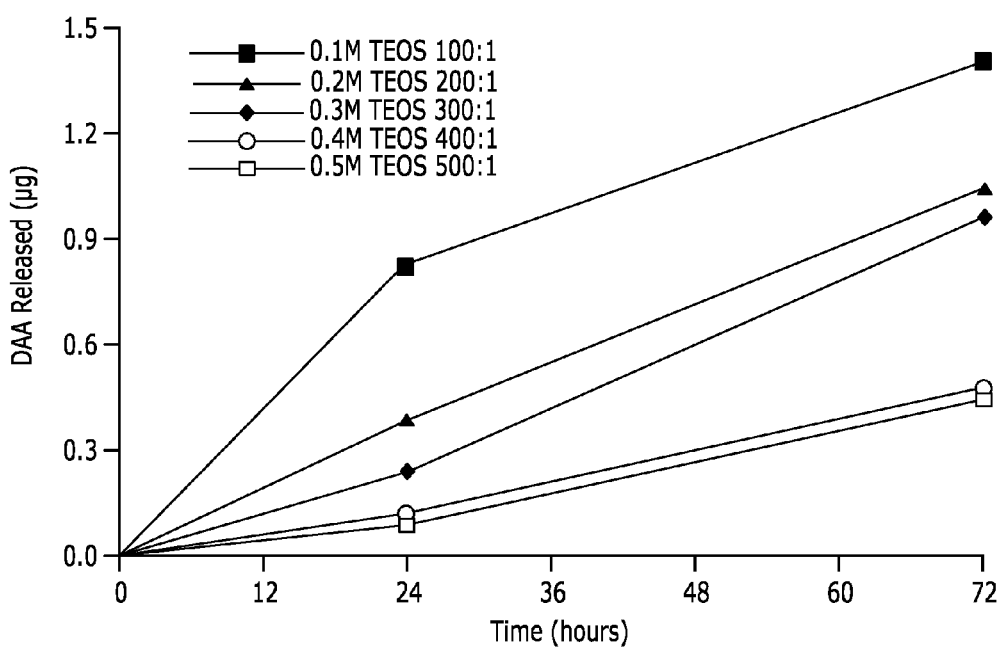

To explore the effects of increasing the amount of TEOS on the rate of elution of DAA-I, increasing amounts, from 0.1-0.5M of TEOS were added to a constant amount of DAA-I (1.25 mg/mL) according to the methods and protocols described above. The stents (9 mm, n=4) were sprayed with each of the solutions as described above, weighed, and the amounts DAA-I eluted over a 24 hour period were compared. FIG. 5A shows the total amount of bioactive material released over 72 hours while FIG. 5B shows elution curves as a function of time. As seen in these FIGS. 5A-5B, increasing the molar ratio of TEOS to the drug significantly delayed the rate of release of the drug into aqueous solution.

Example III

Figure 6:
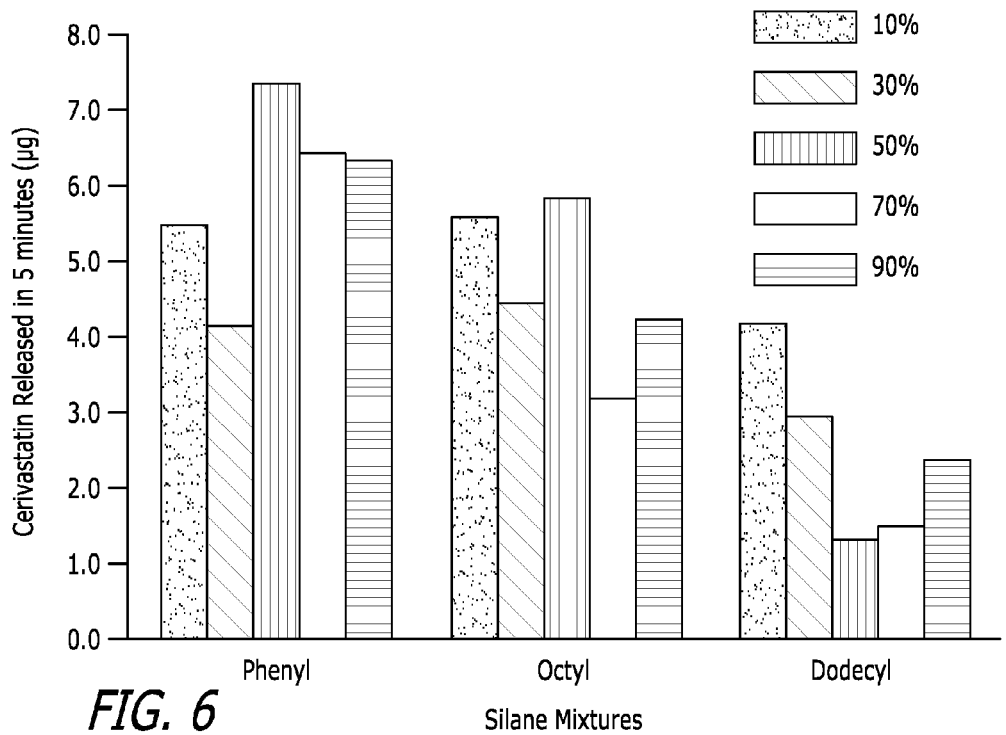
FIG. 6 shows the amount of cervistatin eluted from implantable medical devices coated with sol-gel compositions according to the teachings of the present invention.

Sol-gels composed solely of hydrolyzed TEOS or tetramethoxy silane (MEOS) are relatively hydrophilic and even though they more effectively entrap bioactive materials, they do not provide a chemically compatible environment for most hydrophobic drugs such as paclitaxel, rapamycin, cyclosporin, and other compounds with limited water solubility. To increase the hydrophobic character of the resulting sol-gel a variety of alkylated ethoxy silanes can be added to the sol-gel forming solution. Compounds such as methyl, t-butyl, iso-butyl, hexyl, phenyl, octyl, dodecyl, and octadecyl triethoxy silane can be added to the mixtures at different molar ratios to result in dramatically different sol-gel coatings. The inclusion of such compounds results in significant differences in the ability to incorporate a spectrum of compounds into the gel, and will also affect the rate of their release from the gel into aqueous solutions. An example of such an effect is shown in FIG. 6. Sol-gel solutions were made by mixing varying concentrations of either phenyl, octyl, and dodecyl triethoxy silane from 10-90% with TEOS, with the total concentration of (TEOS+silane) being 0.1M.

Each of the solutions contained an amount of cerivastatin sufficient to coat the stents with 10 μg of drug. After the stents were sprayed and dried, they were separately immersed into 1 mL of water in a polypropylene microfuge tube. Aliquots of the solutions were analyzed for cerivastatin content after five minutes. As seen in FIG. 6, less bioactive material eluted when increasingly more hydrophobic silane was incorporated into the gel. The most effective was dodecyl triethoxy silane, with an optimal content being greater than about 30% and less than about 90%.

Figure 7A:
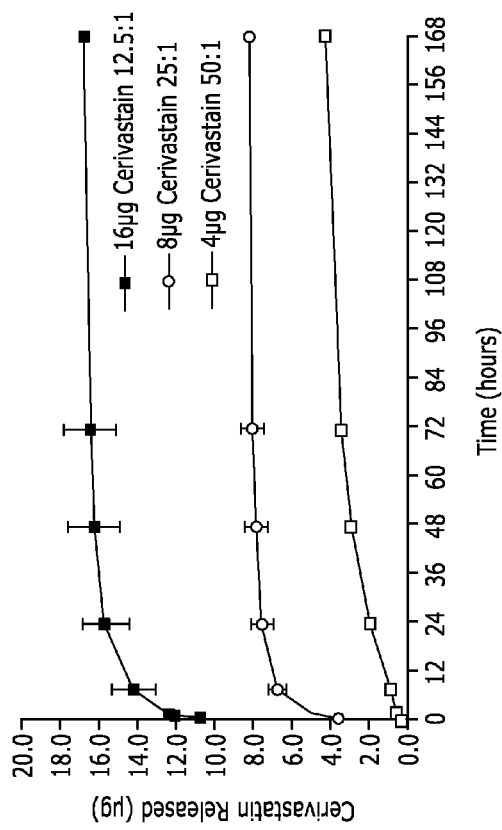
FIGS. 7A-7B show additional cervistatin release profiles.
Figure 7B:
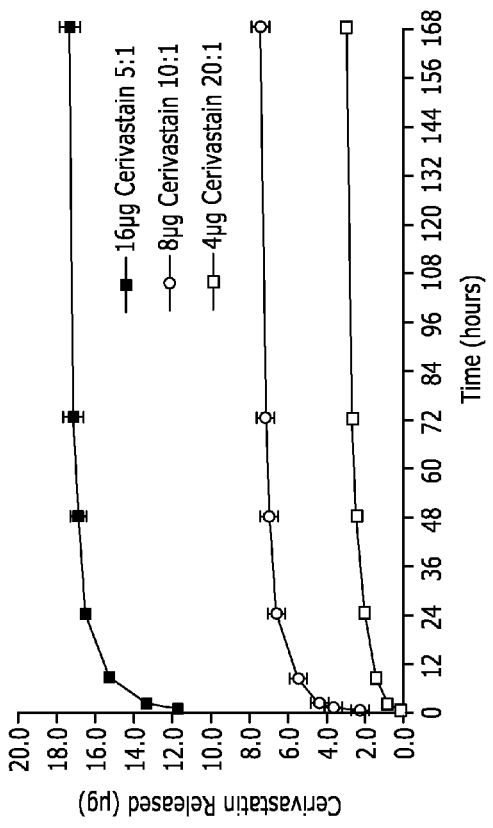

With this knowledge, stents were prepared that directly compared the elution profile of cerivastatin when coated in either 0.5M 100% TEOS or 0.2M 40% dodecyl triethoxy silane/60% TEOS. Interestingly, higher concentrations of the latter composition were not structurally stable. Significant flaking and particle formation was observed on stents coated with 0.3M and higher concentrations of 40% dodecyl triethoxy silane/60% TEOS. The important feature is that the elution curves at 4 μg and 8 μg of cervistatin were equivalent for the two sol-gels, indicating that the inclusion of the hydrophobic silane reduced the total amount of sol-gel precursor needed in the gel to obtain a certain rate of elution (see FIGS. 7A-7B).

Example IV

Figure 8:
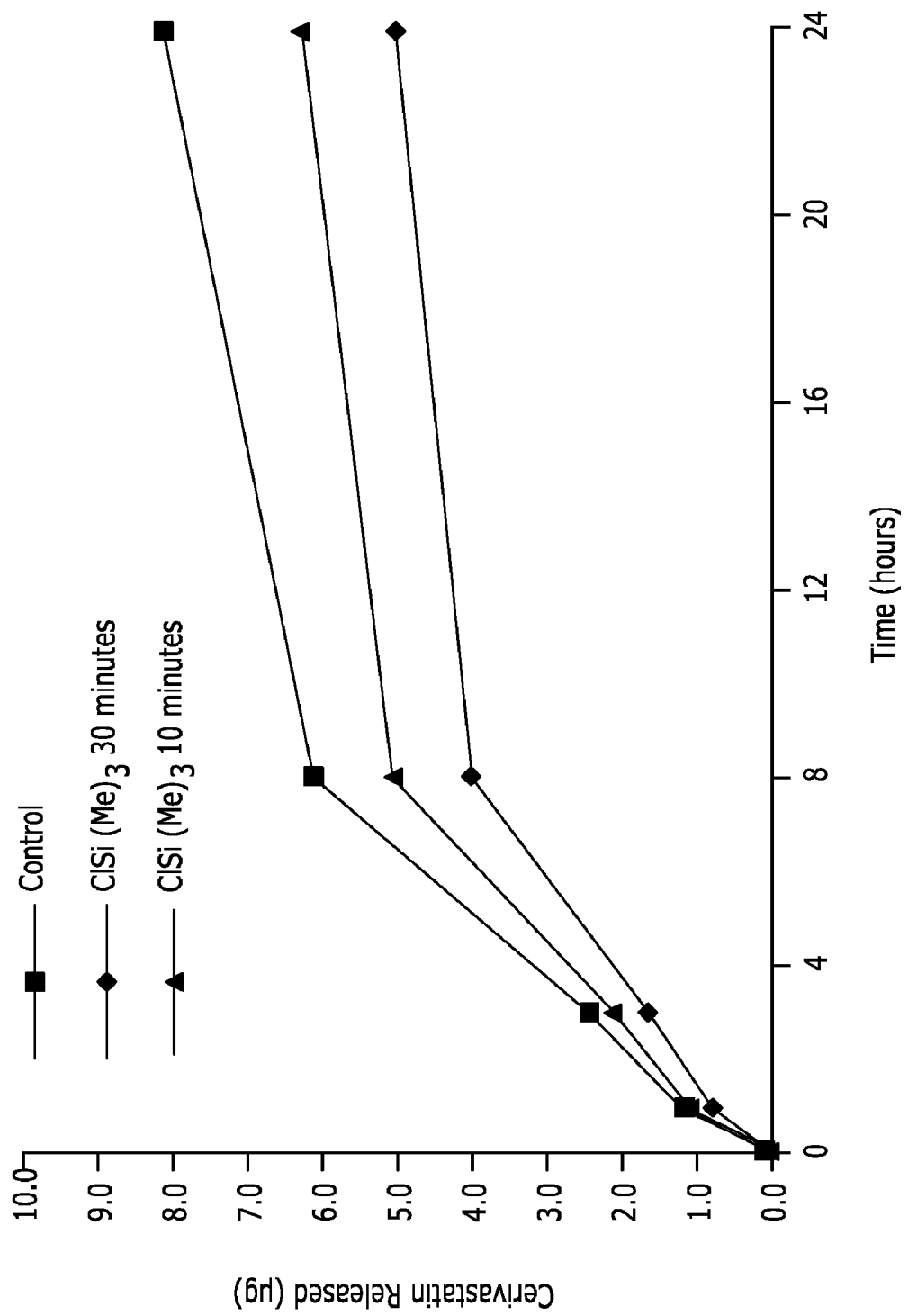
FIG. 8 shows the release profiles of cervistatin from implantable medical devices treated with an organically modified silane according to the teachings of the present invention.

Another non-limiting method of modulating release of bioactive materials from sol-gel matrix compositions is to chemically treat the sol gel with a reactive chlorosilane. In this example, stents were spray coated with 10 μg cerivastatin in 0.5M TEOS and then dried. Next, a second layer of 0.5M TEOS was applied without any bioactive materials. The stents were then treated by immersion in 1M solutions of chlorotrimethyl silane for either about ten minutes or about thirty minutes and then dried in a 40° C. oven overnight. To determine the effect of this "silanation" on the surface of the sol gel, the rate of elution of cerivastatin from these stents was compared to the rate of elution from untreated coated stents. As can be seen in FIG. 8, the modification of the sol gel by the chlorotrimethyl silane reduced the rate of elution with longer exposures having a greater effect on elution profiles.

There are numerous applications of the present invention. One non-limiting example is total hip arthroplasty. Failure of the polymethylmethacrylate (PMMA) cement/metal interface of the femoral component has been recognized as a major cause of aseptic loosening of cemented hip implants. Experimental and numerical studies have concluded that interface debonding can significantly increase the stresses in the surrounding cement mantle, leading to PMMA cracking and overall implant failure.

The present invention is ideal for secure femoral component fixation with a polymeric cement. The sol-gel compositions can be selected according to the implant material of choice. $SiO_2$ films can be deposited on Co—Cr—Mo, while $TiO_2$ films would likely be ideal on Ti6-A14-V components. In combination with the appropriate silane adhesion promoter, excellent bonding between the implant and the precoated PMMA material can be established. Additionally, the roughness of the surface of the sol-gel compositions is several orders of magnitude smaller. This characteristic should be beneficial in preventing debris generation and bone loss.

A $SiO_2$ mesoporous film deposited on Ti6-A14-V alloy substrates and exposed to simulated body fluid have been shown to induce precipitation of hydroxyapatite crystals. However, because of the pore size range, it appears unlikely that the mesoporous film would prove useful in cementless joint replacement applications, as implied in these studies. Pores with sizes in the range of 50-100 µm have been reported as the necessary minimum to allow bone tissue in-growth throughout a porous coating. In contrast, as discussed in the present invention, the mesoporous regime is ideal for accommodating polymer molecular chains.

In one embodiment of the present invention involving the hydrophobic drug paclitaxel, the matrix can be composed by an inorganic oxide derived via sol-gel synthesis (as described above), an ionic or non-ionic surfactant and a block-copolymer, or any combination thereof in any of a wide variety of molar ratios. By appropriately selecting the molar ratio and coating process parameters, this material system can be induced to self-assemble so that the matrix encapsulates the drug and regulates its sustained release via diffusion. The self-assembly process can also involve phase-separation of the matrix ingredients, where the surfactant and/or the block copolymer acts as a template and can guide the assembly of the sol-gel inorganic material (as described above). Subsequent removal of the template component(s) can provide an optional mechanism for regulating the drug release through the resulting interconnected pore channel networks in the inorganic matrix.

In another embodiment, the matrix is composed exclusively of sol-gel silicon oxide and the paclitaxel/TEOS molar ratio is ranging from about 10:1 to about 1:200. For example, a solution with paclitaxel/TEOS molar ratio of about 1:10 and drug concentration of about 5 µg/µL is prepared by dissolving about 5 mg paclitaxel and about 50 µL of TEOS in a solvent composed of about 0.9 mL ethanol and about 50 µL de-ionized water. The stent can be coated with about 2 µL of solution via capillary-assisted painting resulting in about 10 µg of total drug load.

In another embodiment, the paclitaxel (or other bioactive materials) can be first encapsulated in poly-lactic acid (PLA) or block(poly-lactic acid)-block(poly-glycolic acid) (PLGA) polymer spheres, where the polymer/drug molar ratio can be anywhere from about 200:1 to about 1:1 or, in another embodiment, from about 10:1 to about and 3:1. The polymer/drug spheres can be suspended in de-ionized (DI) water so as to form a stable suspension. The spheres can then be deposited on a stent via, for example, spray coating of the aqueous solution, followed by a top coat of sol-gel composition. The biodegradable polymer spheres can provide sustained drug release while the sol-gel composition top coat can provide mechanical strength and improved adhesion of the spheres to the device surface, as well as act as a diffusion barrier to further control the drug elution.

In a specific example, about 40 mg of PLA/paclitaxel spheres (drug concentration at about 18% wt) can be suspended in about 2 mL of DI water. Stents are then spray-coated by about 20 passes through an aerosol-beam obtained by dispensing this solution at a rate of about 40 µL/min and operating the vibrating component at about 2.0 Watts. This procedure results in a total drug load of about 20 µg. Furthermore, a sol-gel silicon oxide top coat can be spray-coated using a hydrolyzed TEOS solution. The hydrolysis can be performed in an aqueous solution, and optionally facilitated by, for example, acidic or basic conditions, agitation via stirring or ultra-sound vibration, the addition of an organic solvent, or any combination of the above. In a specific example the top coat solution has a pH=3 and can be prepared by mixing about 210 µL of TEOS, about 9.25 mL DI water, about 0.5 mL ethanol and about 100 µL of dilute (0.1M) hydrochloric acid (HCl) and vigorously stirring at about 1500 rpm with a magnetic stir-bar for about 1 hour. Top coating involves about 20 stent passes through the spray beam while the solution is dispensed at about 40 µL/min and aerosolized with about 2.0 W of power.

In another example, an intermediate layer of PLA/cerivastatin spheres can be sandwiched between a base coat containing drug and sol-gel composition top coat. This intermediate layer can be obtained by dissolving, for example, about 20 mg of PLA/cerivastatin spheres in about 1 mL DI water and spraying about 20 passes at a dispensing rate of about 40 µL/min and about 1 W aerosolizing power. The purpose of this intermediate layer is to further prolong drug release via interactions of the diffusing molecules with the spheres.

The base coat in these embodiments of the present invention can, but need not, also contain additional bioactive materials. The bioactive materials contained in the base coat can be the same or different from other bioactive materials found in the spheres or optionally in the inorganic sol-gel composition top coat. For instance, the base coat can be a bioactive material-free metallic layer as described in co-pending U.S. Patent Publication No. 2006-0051397 which is incorporated by reference herein for all it discloses regarding the deposition of drug-free metallic layers. Alternatively, the base coat can be a metallic layer with bioactive materials deposited into the metallic layer directly through an electrochemical process or loaded into pores created through the use of an electrochemical process as described in co-pending U.S. Patent Publication Nos. 2006-0062820; 2006-0051397; and 2006-0115512 which are incorporated by reference herein for all they disclose regarding these described techniques. Alternatively, the base coat can be an inorganic sol-gel composition that is bioactive material free, contains bioactive materials within the composition before it is applied to the surface of the medical device, free of bioactive materials until it is applied to the device and bioactive materials loaded into its interconnected channels, or this form of a sol-gel composition can include bioactive materials through both mechanisms. The base coats of the present invention can also be applied according the methodologies described in U.S. Pat. No. 6,730,064 to Ragheb et al., issued May 4, 2004 which is incorporated by reference herein for all that it teaches regarding the application of bioactive material-free and bioactive material-containing coats.

The breadth of the foregoing description should make it clear that the present invention encompasses a wide variety of useful embodiments. These embodiments can comprise a plurality of coatings or layers with the depth of layers only limited by the physical functionality of the device. In certain embodiments, this depth will not exceed about 5 microns. Further, different layers can comprise different bioactive materials, different concentrations of the same or different bioactive materials and/or mixtures of bioactive materials within one or more particular layers. As non-limiting examples, one layer could contain two different bioactive materials, two different layers could contain two different bioactive materials or multiple layers could contain the same bioactive material at different concentrations. As a particular non-limiting example, one device could comprise three layers: the base layer could contain paclitaxel; the middle layer could contain no bioactive materials; and the outer layer top coat could comprise an anti-inflammatory bioactive material such as statin. In this example, the statin would be released quickly upon implantation of the device while the release of the paclitaxel would be delayed. Alternatively, an outer layer top coat can be made hydrophobic with, without limitation, dodecyl silane, to provide a water barrier. As final non-limiting examples of the scope of the present invention, it should be understood that the sol-gel compositions of any layer can be a sol-gel derived inorganic oxide; a sol-gel derived organically modified silane; a hybrid oxide comprising an organically modified silane; and an oxide having mesoscale pores created using a template.

Various adaptations and modifications of the embodiments can be made and used without departing from the scope and spirit of the present invention which can be practiced other than as specifically described herein. The above description is intended to be illustrative, and not restrictive. The scope of the present invention is to be determined only by the claims.

The terms and expressions which have been employed herein are used as terms of description and not of limitation, and there is no intention in the use of such terms and expressions of excluding equivalents of the features shown and described, or portions thereof, it being recognized that various modifications are possible within the scope of the present invention claimed. Moreover, any one or more features of any embodiment of the present invention can be combined with any one or more other features of any other embodiment of the present invention, without departing from the scope of the present invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the present invention otherwise claimed. No language in the specification should be construed as indicating any non-claimed element essential to the practice of the present invention.

Groupings of alternative elements or embodiments of the present invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the patient matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising a structural element and a bioactive material reservoir, wherein said bioactive material reservoir comprises a coating applied to the surface of said structural element wherein said coating comprises one or more layers and wherein at least one of said layers comprises a matrix composition having an inorganic oxide formed using a sol-gel process wherein the inorganic oxide is compounded with an agent that modifies a characteristic of said inorganic oxide selected from the group consisting of hydrophobicity, charge, biocompatibility, mechanical properties, bioactive material affinity, storage capacity, and combinations thereof wherein the environment of said sol-gel process was is tailored to the characteristics of a bioactive material to be incorporated into said matrix composition said tailoring affecting the amount of said bioactive material within said matrix composition once formed and/or the rate of release of said bioactive material into the physiological environment once implanted in a patient.

2. The medical device according to claim 1, wherein said inorganic oxide is selected from the group consisting of an oxide of silicon and an oxide of titanium.

3. The medical device according to claim 1, wherein said modifying agent is an organically modified silane.

4. The medical device according to claim 3, wherein said organically modified silane is selected from the group consisting of alkylsilanes;

methyltrimethoxysilane; methyltriethoxysilane; dimethyldiethoxysilane;

trimethylethoxysilane; vinyltrimethoxysilane; vinyltriethoxysilane; ethyltriethoxysilane;

isopropyltriethoxysilane; butyltriethoxysilane; octyltriethoxysilane;

dodecyltriethoxysilane; octadecyltriethoxysilane; arylfunctional silanes;

phenyltriethoxysilane; aminosilanes; aminopropyltriethoxysilane;

aminophenyltrimethoxysilane; aminopropyltrimethoxysilane; acrylate functional silanes;

methacrylate-functional silanes; acryloxypropyltrimethoxysilane; carboxylate;

phosphonate; ester; sulfonate; isocyanate; epoxy functional silanes; chlorosilanes;

chlorotrimethylsilane; chlorotriethylsilane; chlorotrihexylsilane; dichlorodimethylsilane;

trichloromethylsilane; N,O-Bis (trimethylsilyl)-acetamide (BSA); N,O-Bis (trimethylsilyl) trifluoroacetamide (BSTFA); hexamethyldisilazane (HMOS);

methyltrimethylsilyltrifluoroacetamide (MSTFA); N-methyl-N-(tbutyldimethylsilyl) trifluoroacetamide (MTBSTFA); trimethylchlorosilane (TMCS);

trimethylsilyimidazole (TMSI); and combinations thereof.

5. The medical device according to claim 1, wherein said bioactive material is selected from the group consisting of an anti-restenotic agent, an anti-inflammatory agent, an HMG-CoA reductase inhibitor, an antimicrobial agent, an antineoplastic agent, an angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptive, an analgesic, a bone growth factor, a bone remodeling factor, a neurotransmitter, a nucleic acid, an opiate antagonist and combinations thereof.

6. The medical device according to claim 1, wherein said bioactive material is selected from the group consisting of paclitaxel, rampamycin, everolimus, tacrolimus, sirolimus, des-aspartate angiotensin I, nitric oxide, apocynin, gamma-tocopheryl, pleiotrophin, estradiol, aspirin, atorvastatin, cerivastatin, fluvastatin, lovastatin, pravastatin, rosuvastatin, simvastatin, and combinations thereof.

7. The medical device according to claim 1 wherein said medical device is a device selected from the group consisting of a vascular conduit, a stent, a plate, a screw, a spinal cage, a dental implant, a dental filling, a brace, an artificial joint, an embolic device, a ventricular assist device, an artificial heart, a heart valve, a venous filter, a staple, a clip, a suture, a prosthetic mesh, a pacemaker, a pacemaker lead, a defibrillator, a neurostimulator, a neurostimulator lead, an implantable sensor, and an external sensor.

8. A medical device comprising a structural element and a bioactive material-eluting coating, wherein said bioactive material-eluting coating comprises at least one layer applied over the surface of said medical device wherein said at least one layer is formed using a sol-gel process and comprises an organically modified silane.

9. A medical device according to claim 8 wherein said at least one layer is a base coat and said medical device further comprises a top coat applied over said base coat.

10. The medical device according to claim 9, wherein bioactive material-containing spheres are found in a location selected from the group consisting of within said base coat, within said top coat, between said base coat and said top coat and combinations thereof.

11. The medical device according to claim 10 where said bioactive material-containing spheres comprise of a biodegradable polymer.

12. The medical device according to claim 9, wherein said base coat and/or said top coat comprise a sol-gel inorganic oxide composition.

13. The medical device according to claim 8, wherein said base coat comprises a mesoporous oxide with substantially continuous interconnected channels.

14. A medical device comprising a structural element and a bioactive material-eluting coating, wherein said bioactive material-eluting coating comprises at least two layers with at least one of said layers comprising a matrix composition having an inorganic oxide formed using a sol-gel process wherein the inorganic oxide is compounded with an agent that modifies a characteristic of said inorganic oxide selected from the group consisting of hydrophobicity, charge, biocompatibility, mechanical properties, bioactive material affinity, storage capacity, and combinations thereof wherein the environment of said sol-gel process wasis tailored to the characteristics of a bioactive material to be incorporated into said matrix composition said tailoring affecting the amount of said bioactive material within said matrix composition once formed and/or the rate of release of said bioactive material into the physiological environment once implanted in a patient.

15. The medical device according to claim 14 wherein said at least two layers comprise a base coat and a top coat and said base coat is applied to said surface of said medical device and said top coat is applied over said base coat.

16. The medical device according to claim 14, wherein at least one of said at least two layers comprises a form selected from the group consisting of a solgel oxide layer without bioactive material; a sol-gel oxide layer with bioactive material incorporated in the oxide; a sol-gel oxide compounded with an organically modified silane without bioactive material; a sol-gel oxide compounded with an organically modified silane with bioactive material; an organically modified silane layer without bioactive material; an organically modified silane layer with bioactive material; a mesoporous oxide without bioactive material; a mesoporous oxide with bioactive material incorporated in the oxide; a mesoporous oxide with bioactive material incorporated in the oxide and additional bioactive material loaded into its interconnected channels after the mesoporous oxide is applied to said surface of said medical device; a mesoporous oxide with no bioactive material incorporated in the oxide but with bioactive material loaded into its interconnected channels after the oxide is applied to said surface of said medical device; and a collection of bioactive material containing polymer spheres.

* * * * *